(12) United States Patent
Beger (10) Patent No.: US 6,299,616 B1
(45) Date of Patent: Oct. 9, 2001

(54) ENDOSCOPIC INSERTION APPARATUS

(75) Inventor: Jens Beger, Tuttlingen (DE)

(73) Assignee: Aesculap AG & Co. KG, Tuttlingen (DE)

( * ) Notice: Subject to any disclaimer, the term of this patent is extended or adjusted under 35 U.S.C. 154(b) by 0 days.

(21) Appl. No.: 09/435,103

(22) Filed: Nov. 5, 1999

(30) Foreign Application Priority Data

Nov. 7, 1998 (DE) .............................................. 198 51 370

(51) Int. Cl.[7] ...................................................... A61F 5/00
(52) U.S. Cl. ................................................. 606/86; 606/61
(58) Field of Search .............................. 606/65, 86, 61, 606/104; 623/17.15

(56) References Cited

U.S. PATENT DOCUMENTS

| | | | |
|---|---|---|---|
| 5,236,460 | * 8/1993 | Barber | 623/17.15 |
| 5,368,480 | * 11/1994 | Balfour et al. | 433/141 |
| 5,484,437 | 1/1996 | Michelson | 606/61 |
| 5,527,315 | 6/1996 | Jeanson et al. | 606/61 |
| 5,720,751 | * 2/1998 | Jackson | 606/86 |
| 5,885,299 | * 3/1999 | Winslow et al. | 606/99 |

FOREIGN PATENT DOCUMENTS

| | | |
|---|---|---|
| 297 10 979 U1 | 10/1997 | (DE) . |
| 2 718 943 | 10/1995 | (FR) . |
| WO 95/25487 | 9/1995 | (WO) . |

OTHER PUBLICATIONS

Aesculap Leaflet, "The Spine Masters," SPINE System Evolution, Leaflet No. 0–146–02, May 1998.
Aesculap Leaflet, "The Spine Masters," SOCON Spinal System, Leaflet No. 0–066–02, Jun. 1998.

* cited by examiner

*Primary Examiner*—Gene Mancene
*Assistant Examiner*—Melba Bumgarner
(74) *Attorney, Agent, or Firm*—Barry R. Lipsitz; Douglas M. McAllister (57) ABSTRACT

An endoscopic insertion apparatus for a spinal column implant system is provided having a screwing-in tool and an elongated holding device for holding a bone plate. The implant system essentially comprises at least one anchoring element, a bone plate connected to the anchoring element and at least one connection element for connecting at least two bone plates. The holding device comprises an insertion sleeve and a centering element. The centering element and the insertion sleeve can be connected to one another in a screwing-in position by a coupling mechanism in the direction of a longitudinal axis of the holding device, and the centering element and insertion sleeve can be separated from one another in a centering position. The invention reduces the number of parts used as compared to prior art insertion apparatus and simplifies handling, particularly of the centering element, since the centering element is provided as part of the holding device.

30 Claims, 4 Drawing Sheets

ENDOSCOPIC INSERTION APPARATUS

BACKGROUND OF THE INVENTION

The invention relates to an endoscopic insertion apparatus for a spinal column implant system. The spinal column implant system essentially comprises at least one anchoring element, a bone plate (also referred to herein as "vertebra plate") connected to the anchoring element, and at least one connection element for connecting at least two bone plates. A screwing-in tool is provided for screwing the anchoring element into a bone part to secure the bone plate in place and an elongated holding device is provided for holding the bone plate.

Spinal column implant systems of the type mentioned in the introduction can be used to fix various bone parts relative to one another; in particular, such an implant can be used for fixing adjacent vertebrae of the spinal column. Such an implant system is attached to the bone parts using a plurality of insertion instruments. Particularly where restricted access points are involved, for example in endoscopic operations, endoscopic insertion apparatus of the type mentioned in the introduction is used. A holding device associated with the insertion apparatus is used to hold the bone plate and the connection element connected to the bone plate and to introduce them into the body. The screwing-in tool is then used to screw the anchoring element into the bone part, for example. A similar procedure is carried out with a second anchoring element and a bone plate associated therewith. A connection element, for example a connection rod or a connection plate, is then brought up to the bone plate. The connection element is then fixed relative to the bone plate. In particular, a clamp element can be used to fix the connection element to the bone plate. Such a clamp element is generally very small, and hence there is a risk of losing it in the operating area. It is also difficult to position the clamp element properly relative to the bone plate. In order to simplify positioning the clamp element, centering pieces are used. The centering pieces are arranged (for example screwed on or latched) on the unit comprising the bone plate, the anchoring element and the connection element before the clamp element is introduced. Only when the centering piece has been positioned properly is the clamp element introduced using the clamp element guide tool.

In this procedure, it is disadvantageous that the centering piece has to be introduced as an independent instrument after the anchoring element and the bone plate have already been fixed on the bone part. In addition, a separately attached centering piece requires at least one actuation unit with which it can be introduced and removed again.

SUMMARY OF THE INVENTION

Accordingly, it is an object of the present invention to improve endoscopic insertion apparatus of the type described in the introduction in such a manner that the number of parts used in the apparatus is reduced and that handling, particularly of the centering piece, is simplified.

The invention achieves this object in endoscopic insertion apparatus of the type described in the introduction in that the holding device comprises an insertion sleeve and a centering element. The centering element and the insertion sleeve can be connected to one another in a screwing-in position by a coupling mechanism in the direction of a longitudinal axis of the holding device, and the centering element and the insertion sleeve can be separated from one another in a centering position.

Such a holding device makes it possible to hold the bone plate and the connection element and bring them to the bone part to which the spinal column implant system is to be attached. After the anchoring element has been attached to the bone part using the screwing-in tool, it is no longer necessary to remove the holding device completely and then to use a centering piece. According to the present invention, it is possible to separate the holding device after the anchoring element has been attached. The centering element remains on the unit which comprises the anchoring element and the bone plate and is attached to the bone part, while the insertion sleeve is detached from the centering element. The centering element and the insertion sleeve are connected by a coupling mechanism. This coupling mechanism ensures that the two parts cannot be separated from one another in the axial direction when the anchoring element is attached to the bone part, that is to say that when the holding device is in the screwing-in position. The centering position for introducing the clamp element and the connection element is obtained by separating the insertion sleeve from the centering element. The centering element remains on the spinal column implant system and, in this position, is used for centering of the connection element which is to be introduced and of the clamp element.

It is beneficial if the centering element is formed by an elongated sleeve, at one end of which there is a part of the coupling mechanism. In contrast to centering pieces which are already known, the fact that the centering element of the present invention is designed as a sleeve means that it can perform a centering function both internally and externally. For example, the screwing-in tool can be guided inside the centering element, whereas the clamp element can be guided in the axial direction along the outer peripheral wall of the sleeve in the direction of the spinal column implant. By arranging that part of the coupling mechanism which is located on the centering element at one end of the centering element, the physical size can be significantly reduced. At the same time, the accessibility and functionality of the coupling mechanism between the insertion sleeve and the centering element are simplified.

According to one preferred embodiment of the present invention, provision may be made for the coupling mechanism to be formed by a latch connection having at least one latching lug, formed as a projection, and at least one latching edge, formed as a projection. The latching lug is arranged on a first part of the holding device and the latching edge is arranged on a second part of the holding device. The refinement of the coupling mechanism as a latch connection significantly simplifies handling of the holding device. For release, all that is required is for the latching edge to be moved relative to the latching lug to enable the insertion sleeve to be removed from the centering element. On the other hand, connecting the two parts is particularly easy as they need merely be plugged together. Further the two parts can also be heard to latch when the latching lug slides past the latching edge and engages behind it.

It is particularly advantageous if the latching lug is arranged resiliently on a part of the holding device in the radial direction in relation to the longitudinal axis of the holding device. Although the latching edge could be arranged resiliently in the same way, it suffices if the latching lug is arranged resiliently. This reduces the number of moving parts and increases the lifetime of the instrument.

Although various types of resilient arrangements of the latching lug on the holding device are conceivable, it is particularly beneficial when the latching lug is arranged on a leaf spring, arranged in the peripheral wall of the insertion sleeve, so as to point in the direction of the longitudinal axis of the holding device. The latching lug is thus situated on the inner peripheral wall of the insertion sleeve. In this arrangement, it does not matter whether the leaf spring is integral with the insertion sleeve or is arranged on the insertion sleeve as a separate component, for example.

According to one preferred embodiment of the present invention, provision may be made for a part of the latch connection to be operationally connected to a release projection for releasing the latch connection. With the present invention, it is crucial that the centering element can be separated from the insertion sleeve. Separation can be induced particularly simply if a projection is provided which is operationally connected to the latch connection. This enables one or both moveable parts of the latch connection, for example the latching lug or the latching edge, to be moved relative to the other part. The release projection thus acts as an actuation element for the coupling mechanism.

In this case, it is particularly advantageous if the release projection is arranged on that surface of the leaf spring which points in the direction of the longitudinal axis, and if the release projection is provided with slide surfaces which rise and fall in the axial direction. Such a release projection can be actuated with a particularly low applied force. In addition, this makes it possible for the centering element to be detached from the insertion sleeve by an auxiliary means guided inside the holding device. This prevents inadvertent detachment as a result of the holding device unintentionally bumping into or sliding along an obstacle, for example within the operating area or when the holding device is inserted inside a patient's body.

It is beneficial if the latching edge is formed by an annular projection protruding in the radial direction on the centering element. With the annular projection arranged immovably on the centering element, the stability of the latter is markedly increased even though a resilient arrangement would be quite conceivable. A radial projection is particularly easy to produce on an essentially rotationally symmetrical component, for example using a double annular groove or using a fitted ring which can be permanently connected to the centering element in a variety of ways.

In principle, the invention can provide that the centering element and the insertion sleeve can be connected so as not to rotate. A non-rotating connection between the centering element and the insertion sleeve is particularly desirable if the holding device is intended to be used to transmit torques. This non-rotating connection enables the holding device to be used not only to perform pure holding functions, but also to function as part of a turning tool.

In this case, it is particularly advantageous if the non-rotating connection is formed by a positively locking connection, and if a first part of the positively locking connection is arranged at one end of the insertion sleeve and a second part of the positively locking connection is arranged at one end of the centering element. The positively locking connection provided enables the insertion sleeve and the centering element to be connected without any play therebetween. If the two parts of the positively locking connection are each arranged at one end of those parts of the holding device which can be connected to one another (e.g., the centering element and the insertion sleeve), assembly is simplified significantly. By way of example, it would be conceivable for the two parts to be provided in the form of a plug connection.

In this case, it can be particularly advantageous if the positively locking connection is formed by a polygonal connection having an inner polygon and an outer polygon, and if the axis of symmetry of the polygonal connection is formed by the longitudinal axis of the holding device. Fixing the axis of symmetry in the manner described enables the two parts forming the holding device to be plugged together in the axial direction. In other words, the inner polygon is fitted over the outer polygon or the outer polygon is inserted into the inner polygon. In addition, a polygonal connection affords a defined number of connection positions.

In this case, it is beneficial if the polygonal connection is formed by a hexagonal connection. A hexagonal connection fixes the number of possible insertion positions at six. Hence, merely turning the insertion sleeve ensures that the insertion sleeve is seated onto the centering element in one of six different positions, even without direct visual contact. This is advantageous for endoscopic operations, in particular, in which there is no direct visual contact with the connection point.

According to a further embodiment of the present invention, provision may be made for the other end of the centering element to bear a mounting element for the bone plate. The centering element is part of the holding device, which, as described in the introduction, can be connected to the bone plate and the anchoring element. In contrast to known insertion apparatus, this refinement has the advantage that the centering element is already connected to the bone plate as part of the holding device and no longer has to be connected to the bone plate in an additional operation step after the holding device has been removed. It now suffices for the insertion sleeve to be removed from the centering element, with the result that the centering element is already fixed on the bone plate in the manner described.

In this case, it can be advantageous if the mounting element is formed by a screw thread which corresponds with a screw thread of the bone plate. That end of the holding device which is formed by the centering element can therefore be screwed into part of the bone plate. This can be done before the anchoring element is inserted. To remove the holding device, it is then removed again merely by unscrewing it from this part of the bone plate.

It is particularly advantageous in this case if the screw thread of the centering element is designed as an external thread and the screw thread of the bone plate is designed as an internal thread. The centering element is thus inserted into a part of the bone plate and screwed to this part. This means that this part of the bone plate can be provided with an external thread which corresponds with a thread of the clamp element. The central arrangement of the centering element on the bone plate then enables the clamp element to be brought to the bone plate externally over the centering element and screwed to said bone plate, for example. All other kinds of connections between the clamp element and the bone plate which are known to the person skilled in the art are also conceivable for use with the invention.

In principle, the invention can also provide that the other end of the insertion sleeve can be connected to the screwing-in tool in a screwing-in position, and that the insertion sleeve can be separated from the screwing-in tool in a separating position. Accordingly, the screwing-in tool and the insertion sleeve form an integral instrument in a screwing-in position. In this case, it should be taken into account that the centering element can be attached to the insertion sleeve, but is not required to be attached to it.

According to a particular embodiment of the present invention, provision may be made for the screwing-in tool to have a handle and a tool element. The handle makes the screwing-in tool easy to manage for the surgeon. The tool element can be used for screwing in the anchoring element, for example.

In this case, it is particularly beneficial if the handle can be detached from the tool element, and if the handle has a mount for the tool element. This refinement means that the tool element can be inserted into the handle and connected to it, for example. The detachable connection between the handle and the tool element makes it possible to combine different handles and also different tool elements with one another. In addition, the instrument can be cleaned more easily as a result.

It is particularly advantageous if the handle is formed by a ratchet grip. This means that the surgeon does not need to execute any full turns of the handle when using the screwing-in tool, but instead can move the screwing-in tool in steps in the desired direction by covering a limited rotary angular range, as is usual with ratchets.

In a preferred embodiment of the present invention, a part of the handle can be connected to the tool element so as not to rotate. The non-rotating connection enables direct force transmission in the direction of rotation from the handle to the tool element.

According to an advantageous embodiment of the invention, the screwing-in tool can be locked in the axial direction by a locking device having at least one resilient projection on the screwing-in tool and a corresponding recess on the holding device. In this manner, the screwing-in tool can be particularly easily connected to the holding device and locked. This connection can also be non-rotating, for example, so that torque transmission is possible from the screwing-in tool to the holding device. A resilient projection can be actuated particularly easily and with little applied force. In addition, the screwing-in tool is easily detached and connected to the holding device.

It is advantageous if the other end of the tool element is provided with a polygon which can be inserted in a positively locking manner into a tool mount of the anchoring element. This enables the screwing-in tool to engage in the tool mount of the anchoring element, which makes it possible to screw the anchoring element into the bone part using the screwing-in tool. In this case, the polygon can be designed in various ways, for example as a hexagon.

In addition, provision may be made for the other end of the insertion sleeve to be provided with a polygonal screw drive. In this case, the polygonal screw drive carries out at least two functions. First, the polygon screw drive can be operated using conventional open-ended wrenches. Second, the polygon screw drive can be part of the connection between the insertion sleeve and the screwing-in tool. In a similar way to that between the centering sleeve and the insertion sleeve, the polygonal screw drive and a corresponding polygon on the screwing-in tool can produce a non-rotating connection between the insertion sleeve and the screwing-in tool.

In this case, it is beneficial if the polygonal screw drive is a hexagon. This means that conventional open-ended wrenches can be used for screwing.

In principle, provision can be made for the insertion apparatus to have an actuation member for detaching the insertion sleeve from the centering element. An auxiliary means is required to actuate the coupling mechanism. This is provided by the actuation member, which can be used to act on the coupling mechanism.

In this case, it can be particularly advantageous if the actuation member is formed by a projection which is arranged on the screwing-in tool and interacts with the release projection when the screwing-in tool located in the holding device is withdrawn from the holding device. This refinement allows the screwing-in tool to have a dual function. On the one hand, it can be used for screwing-in and hence as a tool per se. On the other hand, it can be used for detaching the insertion sleeve from the centering element. This is particularly easy if the screwing-in tool is designed such that it can interact with the release projection of the coupling mechanism. This is ensured if the screwing-in tool has a projection. The refinement of the holding device as a sleeve means such that the insertion sleeve can be detached from the centering element by moving the screwing-in tool in the axial direction simplifies operation of the device.

In this case, it is particularly advantageous if the actuation projection is formed by a section of the screwing-in tool whose diameter is larger than the adjacent sections of the screwing-in tool. The diameter of the screwing-in tool can be varied particularly easily. Furthermore, the position for actuating the coupling mechanism can be defined easily and precisely.

It is particularly advantageous if a clamp element guide tool is provided, one end of which has a mount for a clamp element, into which mount the clamp element can be placed symmetrically in a positively locking manner. For finally fixing the connection element of the spinal column implant system on the bone plate and the anchoring element, a clamp element is required. The clamp element guide tool ensures that the clamp element can be brought reliably to the bone plate and the anchoring element without being lost anywhere. The positively locking configuration of the mounting element enables a torque to be transmitted reliably from the clamp element guide tool to the clamp element. The symmetrical configuration of the mount facilitates insertion of the clamp element, which is therefore possible in a variety of ways and in a variety of positions.

In this case, it is particularly beneficial if the clamp element guide tool is designed as a sleeve and the centering element can be inserted into the clamp element guide tool provided with a clamp element from a first end which is provided with the mount. This refinement allows the surgeon to fit the clamp element guide tool with the inserted clamp element over the centering piece and to bring the clamp element guide tool reliably to the bone plate using the centering element.

The clamp element guide tool can be shaped to have no grip, but it is particularly advantageous if a second end of the clamp element guide tool is provided with a handle. The handle considerably facilitates manipulation, and, in addition, the special configuration of the handle makes it possible to limit any torque which may be exerted.

In principle, it is particularly beneficial if the centering element has an axial stop for the bone plate and/or the insertion sleeve. This enables the centering element to be brought to the bone plate in a defined manner and allows the insertion sleeve to be connected to the centering element in a defined manner. In particular, this ensures reliable operation of the coupling mechanism between the insertion sleeve and the centering element.

BRIEF DESCRIPTION OF THE DRAWINGS

The description below of a preferred embodiment of the invention serves for more detailed explanation in conjunction with the drawing, in which.

DETAILED DESCRIPTION OF THE INVENTION

The endoscopic insertion apparatus shown in FIGS. 1 to 5 essentially comprises a holding device 1, a screwing-in tool 2, a socket wrench 3 and a clamp screw key 4.

Figures 1, 2:
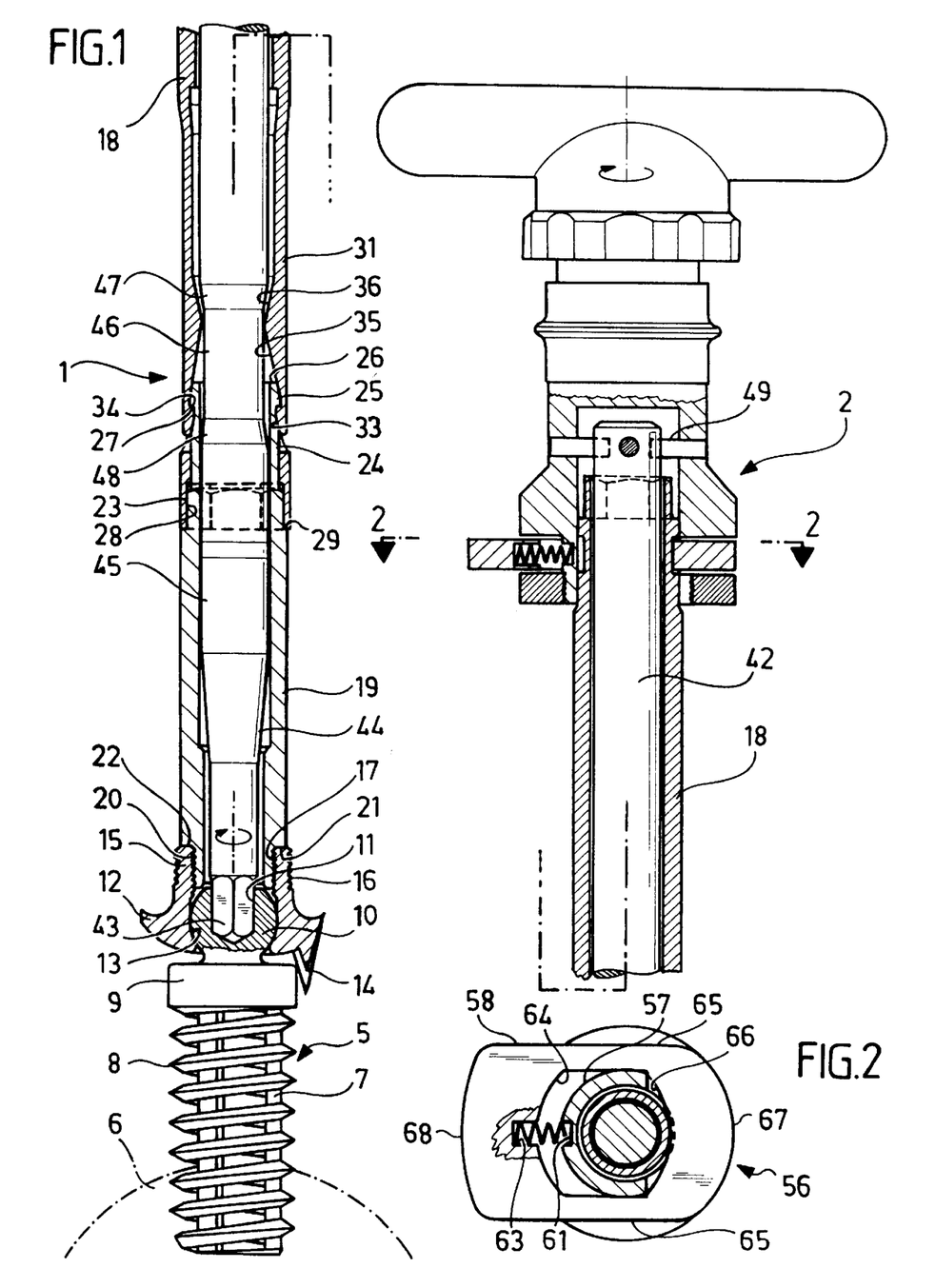
FIG. 1: shows a longitudinal section through a screwing-in tool connected to a holding device when an anchoring element is being screwed into a bone part.
FIG. 2: shows a cross-section along line 2—2 in FIG. 1.

FIG. 1 shows a possible use for the holding device 1 in conjunction with the screwing-in tool 2.

To connect bone parts, for example two vertebrae, a bone anchoring element, for example a hollow screw 5, is screwed into the vertebra 6, which is shown purely schematically in dashed lines. The hollow screw 5 is essentially formed by three support pins 7 of equal length which run parallel to one another. The support pins 7 are arranged in cross-section at the corners of an equilateral triangle and are surrounded by a screw thread 8 over their whole length and are connected to the screw thread 8. One end of the essentially cylindrical hollow screw 5 is provided with a cylindrical termination plate 9 which bears a ball head 10 extending in the axial direction. The ball head 10 contains an internal hexagon 11 in the axial direction, said internal hexagon 11 ending in the manner of a blind hole in the direction of the screw thread 8. The ball head 10 is essentially rotationally symmetrically surrounded by a vertebra plate 12 which has a socket-like ball head mount 13, in which the ball head 10 is mounted. This allows the vertebra plate 12 to turn around the ball head 10 and to be inclined away sideways from the common axis of symmetry. The outer edge of the vertebra plate 12 has spikes 14 pointing in the direction of the hollow screw 5. In addition, the vertebra plate 12 has a sleeve section 15 which extends in the axial direction as an extension of the ball head mount 13. Sleeve section 15 is provided with a clamp screw thread 16 on the outside and with a holding thread 17 on the inside.

To screw in the hollow screw 5, the vertebra plate 12 is connected to the two-part holding device 1. The holding device 1 comprises two parts, a guide sleeve 18 and a sleeve-like centering piece 19. One end of the centering piece 19 of the holding device 1 has a screwing-in holding thread 20 which can be screwed into the holding thread 17 of the vertebra plate 12. The screwing-in holding thread 20 has a somewhat smaller external diameter than the centering piece 19, which forms a stop shoulder 21. The screwing-in holding thread 20 then extends over a length of the centering piece 19 in such a manner that the ball head 10 is still free to move inside the ball head mount 13 when the stop shoulder 21 encounters an end edge 22 of the sleeve section 15.

The internal diameter of the centering piece 19 broadens out after approximately one quarter of its length, starting from the end provided with the screwing-in holding thread 20, such that the wall thickness of the centering piece is reduced to approximately two thirds. The outer surface of the centering piece 19 is completely smooth, starting from the stop shoulder 21 in the axial direction to approximately three quarters of the length of the centering piece 19. This is adjoined by a coupling outer hexagon 23 produced in the outer peripheral wall, the largest external diameter of said coupling outer hexagon 23 being somewhat smaller than the largest external diameter of the centering piece 19. The coupling outer hexagon 23 is adjoined by a further smooth centering sleeve section 24, whose external diameter is reduced somewhat towards the other end of the centering piece 19. The centering piece 19 also has a centering end 26 which is surrounded by an annular bead 25 projecting outwards radially. This annular bead 25 has a latching edge 27 pointing in the direction of the hollow screw 5.

The guide sleeve 18 is connected to the centering piece 19 so as not to rotate and so as to be immovable in the axial direction. The end of the longitudinal guide sleeve 18 which faces the centering piece 19 is provided with a coupling inner hexagon 28 which surrounds the coupling outer hexagon 23 of the centering piece 19 in a positively locking manner. The end of the guide sleeve 18 seated on the centering piece 19 then encounters a coupling stop 29 of the centering piece, which is formed by the transition between the longest smooth section of the centering piece 19 and the coupling outer hexagon 23.

Extending in the axial direction of the guide sleeve 18 are two spring windows 30 which are arranged so as to be staggered by 180° and whose longitudinal edges run parallel to the longitudinal axis of the guide sleeve 18. The spring windows 30 are almost completely filled by a leaf spring 31 which supplements the sleeve wall and is connected to the guide sleeve 18 at one window edge 32 which extends in the circumferential direction of the guide sleeve 18. The free end of the leaf spring 31 has a semi-annular spring bead 33 which extends radially inwards and forms a latching lug 34 being arranged away from the centering piece 19. The thickness of the springs in the radial direction increases in steps, starting from the latching lug 34, which forms an unlocking surface 35. After a maximum wall thickness, this thickness in turn decreases continually and thus forms a locking surface 36. Adjacent to the locking surface 36, the wall thickness of the leaf spring 31 remains essentially constant up to the window edge 32.

The guide sleeve 18 extends over approximately two thirds of its length with a constant internal and external diameter. In the end region of the guide sleeve 18, the outer diameter tapers a little at a taper edge 37. Further towards the end an annular groove 38 is formed in the guide sleeve 18. Directly adjacent to the sleeve end 39, the guide sleeve 18 is provided with a removal hexagon 54 which has the same external diameter as the annular groove 38. This forms an annular coupling projection 40.

The holding device 1 is formed from the centering piece 19 and the guide sleeve 18 as a unit which is connected together so as to be non-rotating. In the connected state, the coupling inner hexagon 28 of the guide sleeve 18 surrounds the coupling outer hexagon 23 of the centering piece 19. The arrangement of the annular bead 25 on the centering piece 19 is provided such that the latching lug 34 on the leaf spring 31 of the guide sleeve 18 engages behind the latching edge 27 when the guide sleeve 18 encounters the coupling stop 29 of the centering piece 19. In this manner, the centering piece 19 and the guide sleeve 18 are connected to one another with virtually no play.

The vertebra plate 12, and hence also the hollow screw 5 which is connected to it, can be held, guided and positioned by the holding device 1.

To screw the hollow screw 5 into the vertebra 6, the screwing-in tool 2 is required.

The screwing-in tool 2 comprises a grip unit 41 and a tool insert 42. The tool insert 42 essentially comprises a cylindrical rod having an external diameter chosen such that the tool insert 42 can be inserted into the guide sleeve 18 and is free to move in it. That end of the tool insert 42 which is remote from the grip unit is shaped as a hexagon 43 which can be inserted in a positively locking manner into the inner hexagon 11 of the ball head 10 of the hollow screw 5. Starting from the hexagon 43, the tool insert 42 merges into the cylindrical rod, which has the smallest diameter over this section. This diameter broadens out continuously to the maximum diameter of the tool insert 42. In this way, a slide surface 44 in the form of a truncated cone is formed. This is adjoined by a tool section 45 having the maximum diameter of the tool insert 42. Further along the tool insert 42, the diameter is reduced over a rod section 46, specifically such that oblique slide surfaces are formed in the transitional regions 47 and 48.

The other end of the tool insert 42 is connected to the grip unit 41 via a coupling device 50 shown schematically by the annular projection 49.

The grip unit 41 is essentially rotationally symmetrical and comprises a mounting unit 51, which can be connected to the tool insert 42 so as not to rotate, and a T-shaped handle 52. The handle 52 is arranged on the mounting unit 51 via a ratchet mechanism which is known to the person skilled in the art. The mounting unit 51 has a rotationally symmetrical cylindrical recess 53 into which the tool insert 42 can be inserted. The recess 53 is additionally prepared to receive that end of the guide sleeve 18 which is provided with the annular groove 38, so that the coupling projection 40 can slide in the recess 53 in the axial direction.

The external diameter of that end of the grip unit 41 which faces the guide sleeve 18 broadens out towards the end. Starting from the maximum diameter, this diameter is reduced in a single step, which forms a slide bearing surface 55 running transversely with respect to the longitudinal axis of the grip unit 41. In this region of the grip unit 41, there is a spring-actuated locking unit 56, as shown in cross-section in FIG. 2. In the region of the single-step reduction in the diameter of the grip unit 41, part of the sleeve-like region of the grip unit 41 is removed, so that a C-shaped mounting guide 57 remains on the grip unit 41. Transversely to the longitudinal axis, a blocking slide 58 is inserted directly adjacent to the slide bearing surface 55. The bottom end of the C-shaped mounting guide 57 is provided with a securing thread 59. A securing nut 60 is screwed onto this securing thread and forms the termination of the grip unit 41. The blocking slide 58 thus slides between the slide bearing surface 55 and the securing nut 60.

The C-shaped region of the mounting guide has a hole 61 formed radially opposite the open section, and a spring 62 is supported in this hole 61 so as to project radially outwards. The other end of the spring 62 is supported in a spring hole 63 provided for it in the blocking slide 58, the axes of symmetry of the hole 61 and the spring hole 63 coinciding. The blocking slide 58 is perforated parallel to the longitudinal axis of the grip unit 41. In the spring-loaded state, the blocking slide 58 locks the guide sleeve 18 located in the recess 53. The blocking slide 58 then encounters one side of the annular groove 38 in the guide sleeve 18 with a semicircular inner edge 66 of the perforation 64. In this position, a semicircular outer edge 67 of the blocking slide 58 is matched to the diameter of the grip unit 41. Two further side edges 65 of the blocking slide 58 run parallel to the axis of symmetry of the spring 62. The pressure edge 68 opposite the outer edge 67 has a significantly larger radius of curvature and serves to actuate the blocking slide 58 by pressing onto the pressure edge 68.

Figure 4:
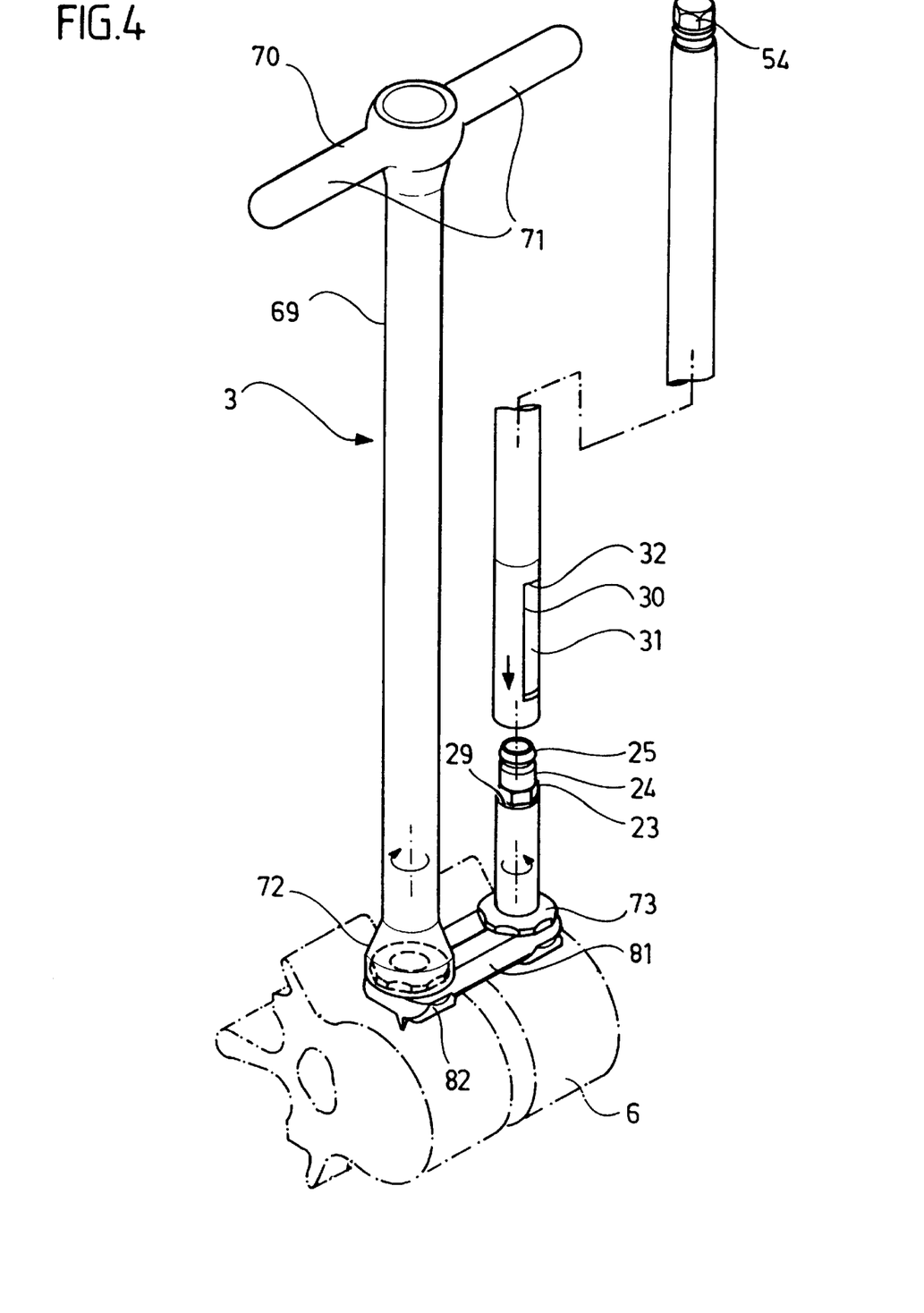
FIG. 4: shows a perspective view of a clamp element being fixed using a clamp element guide tool and of the centering element being removed from the bone plate.

A further component of the endoscopic insertion apparatus which is provided is the socket wrench 3, as shown in FIG. 4. This essentially comprises an elongated socket sleeve 69. One end of the socket sleeve 69 has a key grip 70 which runs transversely with respect to the longitudinal axis and is formed by two radially projecting grip rods 71. At the opposite end, the socket sleeve 69 is extended by a rotationally symmetrical nut mount 72 whose inside is shaped such that it can surround a clamp nut 73 in a positively locking manner. The clamp nut 73 is therefore situated in a rotationally symmetrical arrangement with respect to the longitudinal axis of the socket sleeve 69.

Figure 5:
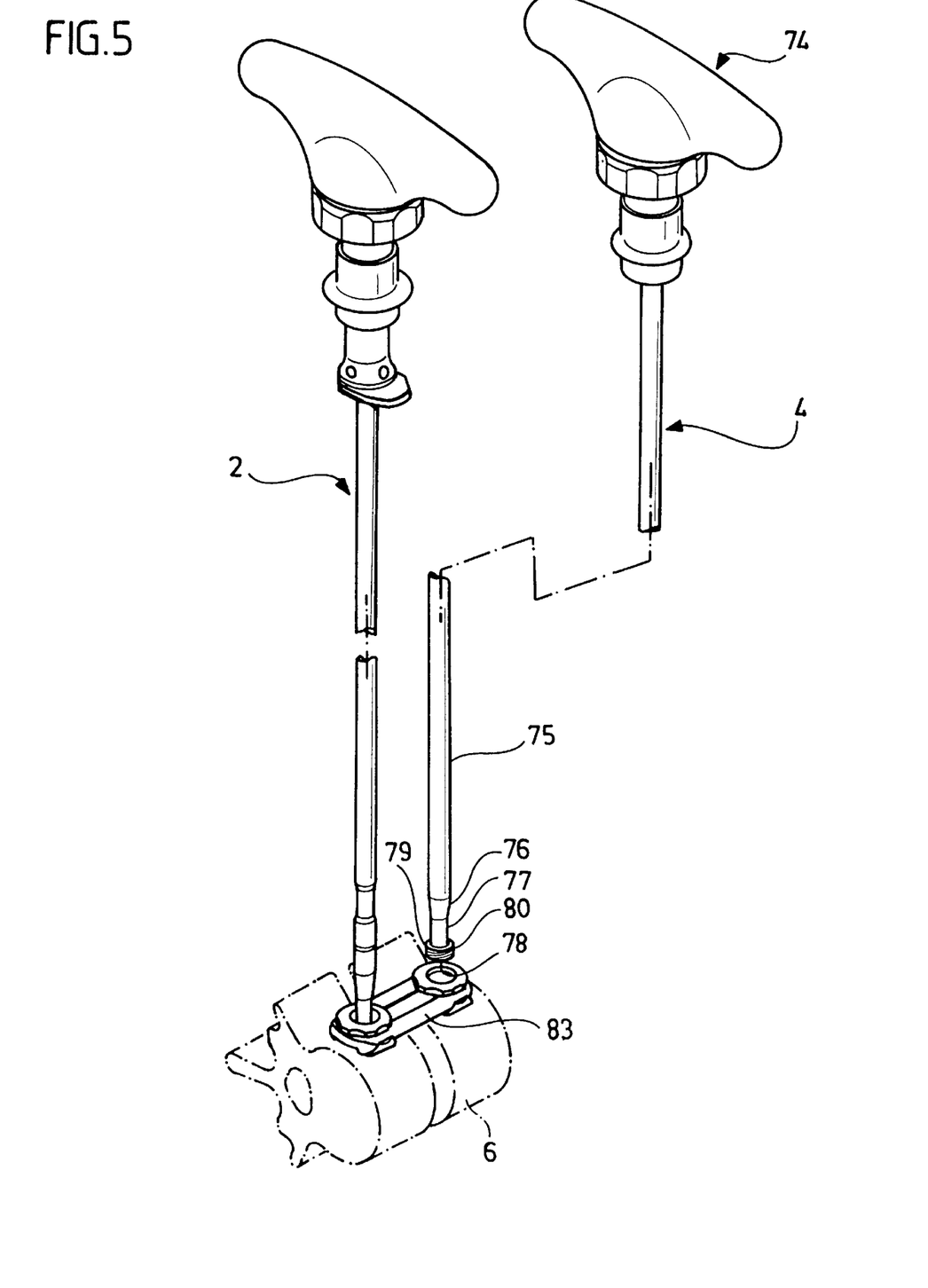
FIG. 5: shows a perspective view of a screwing-in tool when the anchoring element is being fixed in the bone part and of a turning tool when the anchoring element is being finally fixed relative to the bone plate by means of a clamp screw.

A further instrument of the insertion apparatus which is provided is the clamp screw key 4. This essentially resembles the screwing-in tool 2 and accordingly comprises a handle 74 and a screwing tool 75. The screwing tool 75 and the handle 74 are connected to one another detachably. This connection can be designed in a similar manner to the connection between the tool insert 42 and the grip unit 41 of the screwing-in tool 2. Similarly, the handle 74 can be designed as a ratchet grip. That end of the screwing tool 75 which is remote from the handle 74 has a taper 76 which merges into a cylindrical end section 77. The end of the end section 77 bears a shaping tool 78 (not shown in further detail). This is shaped, for example as an outer hexagon, such that it can engage in a complementary recess in a clamp screw 79 having a clamp thread 80 on the outside which can be screwed into the holding thread 17 of the sleeve section 15 of the vertebra plate 12 of the hollow screw 5.

The use of the endoscopic insertion apparatus will now be described below with the aid of FIGS. 1 to 5 for the case of relative fixing of two vertebrae 6.

For this, the holding device 1 and the screwing-in tool 2 must first be prepared. In a first step, the hollow screw 5 is screwed to the centering piece 19 using the holding thread 17 provided for this. The screwing-in holding thread 20 of the centering piece is screwed into the holding thread 17 until the centering piece 19 encounters the end edge 22 of the sleeve section 15 with the stop shoulder 21.

Next, the guide sleeve 18 is connected to the centering piece 19. For this purpose, that end of the guide sleeve 18 which has the leaf spring 31 is guided in the axial direction over that end of the centering piece 19 which has the annular bead 25. The configuration of the ends of the centering piece 19 and of the guide sleeve 18 with a coupling outer hexagon 23 and a coupling inner hexagon 28 produces six angle dependent coupling positions. Accordingly, the guide sleeve 18 needs to be turned relative to the centering piece 19 such that the coupling inner hexagon 28 engages completely around the coupling outer hexagon 23. In the course of this axial movement of the guide sleeve 18 towards the centering piece 19, the spring bead 33 of the leaf spring 31 slides on the annular bead 25, which causes the leaf spring 31 to open outwards in the radial direction. As soon as the end of the guide sleeve 18 encounters the coupling stop 29 of the centering piece 19, the leaf spring 31 relaxes because the latching lug 34 slides back behind the latching edge 27 and is latched there. The holding device 1 is thus completely assembled, and the guide sleeve 18 is connected to the centering piece 19 so as not to rotate and so as to be fixed in the axial direction.

The screwing-in tool 2 can now be inserted into the holding device 1. This holding device was previously assembled from the grip unit 41 and the tool insert 42 using the coupling device 50. The screwing-in tool 2 is now pushed into the holding device 1 until the blocking slide 58 encounters the sleeve end 39. The exertion of pressure onto the pressure edge 68 of the blocking slide 58 moves the blocking slide 58 transversely with respect to the longitudinal axis of the screwing-in tool, and this means that the screwing-in tool 2 can now be pushed further forward into the holding device 1. If an axial position as shown in FIG. 1 is reached, the pressure on the blocking slide 58 is reduced and the inner edge 66 of the blocking slide 58 slides forward into the annular groove 38. In this way, the grip unit 41 is connected to one end of the guide sleeve 18 and is fixed in the axial direction. While the screwing-in tool 2 was being inserted into the holding device 1, which already has the hollow screw 5 screwed onto it, the hexagon 43 slid into the inner hexagon 11 of the ball head 10 of the hollow screw 5.

The preparations described above have now produced a unit comprising the holding device 1, the screwing-in tool 2 and the hollow screw 5. The hollow screw 5 can now be attached to a vertebra 6 and can be screwed into the vertebra 6 by turning the hand grip 52 of the screwing-in tool 2. For this, the hand grip 52 has to be turned clockwise out of sight of the surgeon, as indicated in FIG. 1. The hollow screw 5 is now screwed into the vertebra 6 to an extent such that the spikes 14 have not yet penetrated the vertebra 6.

Figure 3:
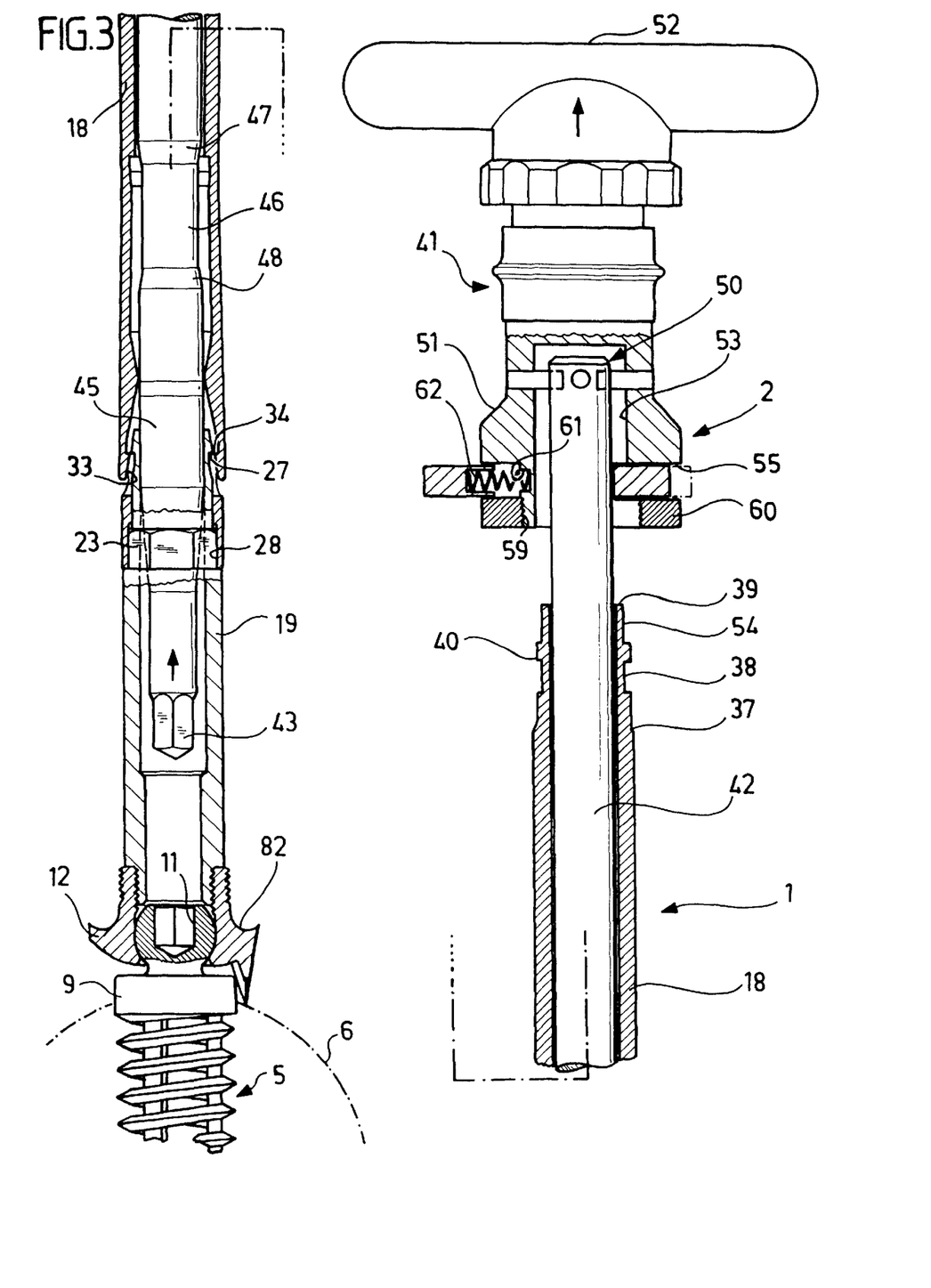
FIG. 3: shows a sectional view similar to FIG. 1, but after the screwing-in tool has been separated from the holding device.

In a subsequent step, the guide sleeve 18 is separated from the centering piece 19, specifically by withdrawing the screwing-in tool 2 from the holding device 1. To detach the screwing-in tool 2 from the guide sleeve 18, the blocking slide 58 must first be released from its locked position. This is done, in turn, by exerting pressure onto the pressure edge 68. The screwing-in tool 2 can now be withdrawn from the guide sleeve 18 in the axial direction. During this movement, the transitional region 48 slides on the unlocking surface 35 of the tool insert 42, which stretches the leaf spring 31 radially outwards. This causes the latching lug 34 to move out from its latching position behind the latching edge 27 and release the latter, as shown in FIG. 3. The guide sleeve 18 and the centering piece 19 are now unlocked and can be separated from one another in the axial direction. The centering piece 19 remains on the hollow screw 5.

A further centering piece 19 is once again assembled using the withdrawn unit comprising the screwing-in tool 2 and the guide sleeve 18 in the manner described, after it has been connected to a further hollow screw 5. Using the procedure which is already known, the further hollow screw 5 is screwed into an adjacent vertebra 6. The guide sleeve 18 is then separated from the centering piece 19, in the manner which is already known, by withdrawing the screwing-in tool 2.

The two centering pieces can now be used to thread a connection plate 81 and thus place it into the connection plate mounts 82 so as to connect the two hollow screws 5. Instead of a connection plate 81, two connection rods 83 can also be provided.

To fix the connection plate 81 or the connection rods 83 to the vertebra plates 12 of the hollow screws 5, a clamp nut 73 is placed into the nut mount 72 of the socket wrench 3. The socket wrench 3 is now guided, together with the clamp nut 73, over the centering piece 19, and the internal thread of the clamp nut 73 is screwed onto the clamp screw thread 16 and firmly tightened. The socket wrench 3 is then withdrawn and fitted with another clamp nut 73. The socket wrench 3 is inserted over the further centering piece 19 in a similar way and the clamp screw 73 is first screwed loosely to the vertebra plate 12.

If appropriate, a traction apparatus (not shown) can be used at this stage to set the distance between the two vertebrae 6 as desired. As soon as the desired distance has been achieved, the socket wrench 3 is used to screw the other clamp nut 73 firmly to the second vertebra plate 12 as well. The two vertebrae 6 are now firmly connected to one another via the connection plate 81.

To bring the hollow screws 5 into their final position, the centering piece 19 must first be removed. For this, the guide sleeve 18 is fitted over the centering piece 19 and latched to it, as described further above. The guide sleeve 18 and the centering piece 19 are thus connected to one another so as not to rotate. An open-ended wrench (not shown) can be used to remove the holding device 1 from the hollow screw 5 by means of the removal hexagon 54 by turning the holding device 1 anticlockwise.

If the two centering pieces 19 are removed from the hollow screws 5 in this way, the screwing-in tool 2 can be engaged in the inner hexagon 11 of the ball head 10 of the hollow screw 5 again. The hollow screw 5 is now screwed into the vertebra 6 until the spikes 14 penetrate the vertebra 6 and the vertebra plate 12 bears against the vertebra 6.

To prevent further rotation of the vertebra plate 12 relative to the ball head 10, a clamp screw 79 is placed onto the shaping tool 78 of the clamp screw key 4 and 15 screwed to the vertebra plate 12. A clamp thread 80 of the clamp screw 79 then engages in the holding thread 17 of the sleeve section 15 of the vertebra plate 12. The two vertebrae 6 are finally fixed when the two hollow screws 5 are provided with a clamp screw 79 which is tightened so firmly that relative movement of the vertebra plate 12 and the ball head 10 becomes impossible. The clamp screw key 4 can then be removed from the patient's body again.

What is claimed is:

1. Endoscopic insertion apparatus for a spinal column implant system, said implant system having at least one anchoring element, a bone plate connected to the anchoring element, and at least one connection element for connecting at least two bone plates, said apparatus comprising:

a screwing-in tool; and an elongated holding device for holding the bone plate, wherein:

the holding device comprises an insertion sleeve and a centering element, the centering element and the insertion sleeve are connectable to one another in a screwing-in position by a coupling mechanism in the direction of a longitudinal axis of the holding device, the centering element and the insertion sleeve are separable from one another in a centering position, the coupling mechanism comprises a latch connection having at least one projecting latching lug and at least one projecting latching edge, and said latching lug being arranged on one of said centering element or said insertion sleeve and the latching edge is arranged on the other of said centering element or said insertion sleeve.

2. Endoscopic insertion apparatus according to claim 1, wherein the centering element is formed by an elongated sleeve, at one end of which there is a part of the coupling mechanism.

3. Endoscopic insertion apparatus according to claim 1, wherein the latching lug is arranged resiliently on one of said centering element or said insertion sleeve in a radial direction in relation to the longitudinal axis of the holding device.

4. Endoscopic insertion apparatus according to claim 1, wherein the latching lug is arranged on a leaf spring, said leaf spring being arranged in the peripheral wall of the insertion sleeve, so as to point in the direction of the longitudinal axis of the holding device.

5. Endoscopic insertion apparatus according to claim 4, wherein the latch connection is operationally connected to a release projection for releasing the latch connection.

6. Endoscopic insertion apparatus according to claim 5, wherein:
   the release projection is arranged on a surface of the leaf spring which points in the direction of the longitudinal axis, and
   the release projection is provided with slide surfaces which rise and fall in the axial direction.

7. Endoscopic insertion apparatus according to claim 1, wherein the latching edge is formed by an annular projection protruding in the radial direction on the centering element.

8. Endoscopic insertion apparatus according to claim 1, wherein the centering element and the insertion sleeve are connectable so as not to rotate.

9. Endoscopic insertion apparatus according to claim 1, wherein:
   the coupling mechanism comprises a positively locking non-rotating connection between the centering element and the insertion sleeve.

10. Endoscopic insertion apparatus according to claim 9, wherein:
    the positively locking connection is formed by a polygonal connection having an inner polygon and an outer polygon, and
    an axis of symmetry of the polygonal connection is formed by the longitudinal axis of the holding device.

11. Endoscopic insertion apparatus according to claim 10, wherein the polygonal connection is formed by a hexagonal connection.

12. Endoscopic insertion apparatus according to claim 1, wherein an end of the centering element bears a mounting element for the bone plate.

13. Endoscopic insertion apparatus according to claim 12, wherein the mounting element is formed by a screw thread which corresponds with a screw thread of the bone plate.

14. Endoscopic insertion apparatus according to claim 13, wherein the screw thread of the mounting element is designed as an external thread and the screw thread of the bone plate is designed as an internal thread.

15. Endoscopic insertion apparatus according to claim 1, wherein:
    an end of the insertion sleeve is connectable to the screwing-in tool in a screwing-in position, and
    the insertion sleeve is separable from the screwing-in tool in a separating position.

16. Endoscopic insertion apparatus according to claim 1, wherein the screwing-in tool has a handle and a tool element.

17. Endoscopic insertion apparatus according to claim 16, wherein the handle has a mount for the tool element and is detachable from the tool element.

18. Endoscopic insertion apparatus according to claim 16, wherein the handle is formed by a ratchet grip.

19. Endoscopic insertion apparatus according to claim 16, wherein a part of the handle is connectable to the tool element so as not to rotate.

20. Endoscopic insertion apparatus according to claim 16, wherein the screwing-in tool is lockable to the holding device in the axial direction by a locking device having at least one resilient projection on the screwing-in tool and a corresponding recess on the holding device.

21. Endoscopic insertion apparatus according to claim 16, wherein an end of the tool element is provided with a polygon which is insertable in a positively locking manner into a tool mount of the anchoring element.

22. Endoscopic insertion apparatus according to claim 1, wherein an end of the insertion sleeve is provided with a polygonal screw drive.

23. Endoscopic insertion apparatus according to claim 22, wherein the polygonal screw drive is a hexagon.

24. Endoscopic insertion apparatus according to claim 1, wherein the insertion apparatus has an actuation member for detaching the insertion sleeve from the centering element.

25. Endoscopic insertion apparatus according to claim 24, wherein the actuation member is formed by a projection which is arranged on the screwing-in tool and interacts with a release projection on the holding device when the screwing-in tool located in the holding device is withdrawn from the holding device.

26. Endoscopic insertion apparatus according to claim 25, wherein the actuation projection is formed by a section of the screwing-in tool whose diameter is larger than adjacent sections of the screwing-in tool.

27. Endoscopic insertion apparatus according to claim 1, further comprising:
    a clamp element guide tool having a first end which has a mount for a clamp element, wherein the clamp element is placeable symmetrically in said mount in a positively locking manner.

28. Endoscopic insertion apparatus according to claim 27, wherein:
    the clamp element guide tool comprises a sleeve, and
    the centering element is insertable into the clamp element guide tool.

29. Endoscopic insertion apparatus according to claim 27, wherein a second end of the clamp element guide tool is provided with a handle.

30. Endoscopic insertion apparatus according to claim 1, wherein the centering element has an axial stop for at least one of the bone plate and the insertion sleeve.

* * * * *